US00RE49055E

(19) United States
(12) Reissued Patent
Ukawa et al.

(10) Patent Number: US RE49,055 E
(45) Date of Reissued Patent: May 3, 2022

(54) VENOUS PRESSURE MEASUREMENT APPARATUS

(71) Applicant: NIHON KOHDEN CORPORATION, Tokyo (JP)

(72) Inventors: Teiji Ukawa, Tokyo (JP); Tsuneo Takayanagi, Tokyo (JP); Haruka Morimoto, Tokyo (JP); Tatsuo Nishihara, Tokyo (JP); Tatsuo Yoshida, Tokyo (JP); Shiro Adachi, Tokyo (JP); Mitsushi Hyogo, Tokyo (JP)

(73) Assignee: NIHON KOHDEN CORPORATION, Tokyo (JP)

(21) Appl. No.: 16/921,509

(22) Filed: Jul. 6, 2020

Related U.S. Patent Documents

Reissue of:
(64) Patent No.: 9,743,846
Issued: Aug. 29, 2017
Appl. No.: 13/433,708
Filed: Mar. 29, 2012

U.S. Applications:
(62) Division of application No. 16/397,760, filed on Apr. 29, 2019, now Pat. No. Re. 48,076, which is an application for the reissue of Pat. No. 9,743,846.

(30) Foreign Application Priority Data

Mar. 30, 2011 (JP) ..... 2011-074839

(51) Int. Cl.
*A61B 5/02* (2006.01)
*A61B 5/022* (2006.01)
(Continued)

(52) U.S. Cl.
CPC ..... *A61B 5/02225* (2013.01); *A61B 5/02133* (2013.01); *A61B 5/02141* (2013.01);
(Continued)

(58) Field of Classification Search
CPC . A61B 5/0222; A61B 5/0225; A61B 5/02133; A61B 5/02141; A61B 5/02422; A61B 5/7246; A61B 5/7289
See application file for complete search history.

(56) References Cited

U.S. PATENT DOCUMENTS 3,590,809 A * 7/1971 London ..... 600/487
6,432,061 B1 * 8/2002 Nissila ..... A61B 5/02152 600/485
(Continued)

FOREIGN PATENT DOCUMENTS

EA 003497 6/2003
GB 1598984 A 9/1981
(Continued)

OTHER PUBLICATIONS

Official Notice of Reason for Refusal dated Aug. 5, 2014 for Japanese Patent Application No. 2011-074839.
Extended European Search Report dated Aug. 8, 2012.

*Primary Examiner* — Robert L Nasser
(74) *Attorney, Agent, or Firm* — Sughrue Mion, PLLC

(57) ABSTRACT

A non-invasive venous pressure measurement apparatus is provided, including: a first cuff attached to a portion including a vein and an artery in a living body; a pressure control unit that changes a first applied pressure applied by the cuff to the portion; a pulse wave detection unit that detects a pulse wave from a pressure received by the cuff from the portion; another pulse wave detection unit that detects another pulse wave including at least an arterial pulse wave in another portion of the living body; an analyzing unit that analyzes a correlation between the two pulse waves, which are changed as the applied pressure is changed by the pressure control unit changes; and a venous pressure calculation unit that calculates a venous pressure based on the
(Continued)

applied pressure and a result of analysis by the analyzing unit.

2 Claims, 11 Drawing Sheets

(51) Int. Cl.
*A61B 5/021* (2006.01)
*A61B 5/024* (2006.01)
*A61B 5/00* (2006.01)

(52) U.S. Cl.
CPC ..... *A61B 5/02422* (2013.01); *A61B 5/6824* (2013.01); *A61B 5/7246* (2013.01); *A61B 5/7289* (2013.01)

(56) References Cited

U.S. PATENT DOCUMENTS

| | | | | |
|---|---|---|---|---|
| 6,447,457 | B1 | 9/2002 | Forstner et al. | |
| 7,118,534 | B2 | 10/2006 | Ward et al. | |
| 2003/0109772 | A1 | 6/2003 | Mills | |
| 2006/0020216 | A1* | 1/2006 | Oishi et al. | 600/500 |

FOREIGN PATENT DOCUMENTS

| | | | | | |
|---|---|---|---|---|---|
| GB | 1 598 984 | | * | 9/1981 | A61B 5/02 |
| JP | 2001-309894 | | | 11/2001 | |
| JP | 2001-309894 | A | | 11/2001 | |
| JP | 2010-279654 | | | 12/2010 | |
| JP | 2010279654 | A | | 12/2010 | |
| RU | 2107456 | | | 3/1998 | |
| RU | 2107456 | C1 | | 3/1998 | |

* cited by examiner

VENOUS PRESSURE MEASUREMENT APPARATUS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

[This application] *More than one reissue application has been filed for the reissue of U.S. Pat. No. 9,743,846. The reissue applications are the present application, which* is [based on] *a divisional of U.S. application Ser. No. 16/397,760 filed Apr. 29, 2019, in the U.S. Patent and Trademark Office, and U.S. application Ser. No. 16/397,760, which is also a reissue application of U.S. Pat. No. 9,743,846, which was filed as U.S. application Ser. No. 13/433,708 on Mar. 29, 2012, in the U.S. Patent and Trademark Office, which claims priority from* Japanese Patent Application No. 2011-074839 filed on Mar. 30, 2011, the contents of which are [incorporated] herein *incorporated* by reference.

BACKGROUND

1. Technical Field

Embodiments include a venous pressure measurement apparatus, and particularly, to a venous pressure measurement apparatus for non-invasively measuring a mean venous pressure.

2. Description of Related Art

The venous pressure in the vicinity of the right atrium is called a central venous pressure, which indicates a cardiac preload used as an important index to recognize the circulatory dynamics.

The central venous pressure can be invasively measured by inserting a catheter into the vicinity of the right atrium. However, recently, a venous pressure measurement apparatus capable of non-invasively measuring the central venous pressure with a reduced burden to the patient has been developed.

In Unexamined Japanese Patent Publication No. 2010-279654 ("JP 2010-279654"), there is disclosed as related art of the non-invasive venous pressure measurement, in which the artery and the vein are occluded by a cuff applied to the upper arm once, after that, the occlusion of the artery and the vein is sequentially released by gradually reducing the cuff pressure, and, at the same time, these are detected by using a gray scale value of a projection image obtained by irradiating infrared rays onto the leading edge of the antebrachial region, so that the venous pressure is measured based on the cuff pressure when the congestion is released.

However, in "JP 2010-279654", it does not teach that the venous pressure is measured while a living body is under natural conditions since the vein is congested once, and the venous pressure is measured when the venous blood starts to flow from the congested state. In addition, instruments to irradiate infrared rays and the infrared sensor are necessary.

SUMMARY

A non-invasive venous pressure measurement apparatus capable of measuring the venous pressure using simple so instruments based on a change of the venous pulse wave while the living body is under natural condition is provided.

The aforementioned problems of measuring venous pressure are addressed by the following configuration.

In one aspect there is provided a venous pressure measurement apparatus including: a first cuff attached to in a first portion including a vein and an artery in a living body; a pressure control unit that changes a first applied pressure applied by the first cuff to the first portion; a first pulse wave detection unit that detects a first pulse wave from the pressure received by the first cuff from the first portion; a second pulse wave detection unit that detects a second pulse wave including at least an arterial pulse wave in a second portion different from the first portion of the living body; an analyzing unit that analyzes a correlation between the second pulse wave detected by the second pulse wave detection unit and the first pulse wave detected by the first pulse wave detection unit, which are changed as the first applied pressure is changed by the pressure control unit; and a venous pressure calculation unit that calculates a venous pressure based on the first applied pressure and a result of analysis by the analyzing unit.

In another aspect there is provided a venous pressure measurement apparatus including: a cuff attached to a portion including a vein and an artery in a living body; a pressure control unit that changes an applied pressure applied by the cuff to the portion; a pulse wave detection unit that detects a pulse wave from a pressure received by the cuff from the portion; and a venous pressure calculation unit that calculates a venous pressure based on the applied pressure and the pulse wave detected by the pulse wave detection unit, the pulse wave being changed as the applied pressure is changed by the pressure control unit.

The objects, features, and characteristics presented, other than those set forth above, will become apparent from the description given herein below with reference to preferred embodiments illustrated in the accompanying drawings.

DETAILED DESCRIPTION

Hereinafter, a venous pressure measurement apparatus according to embodiments of this invention will be described in detail with reference to the accompanying drawings.

Figure 1:
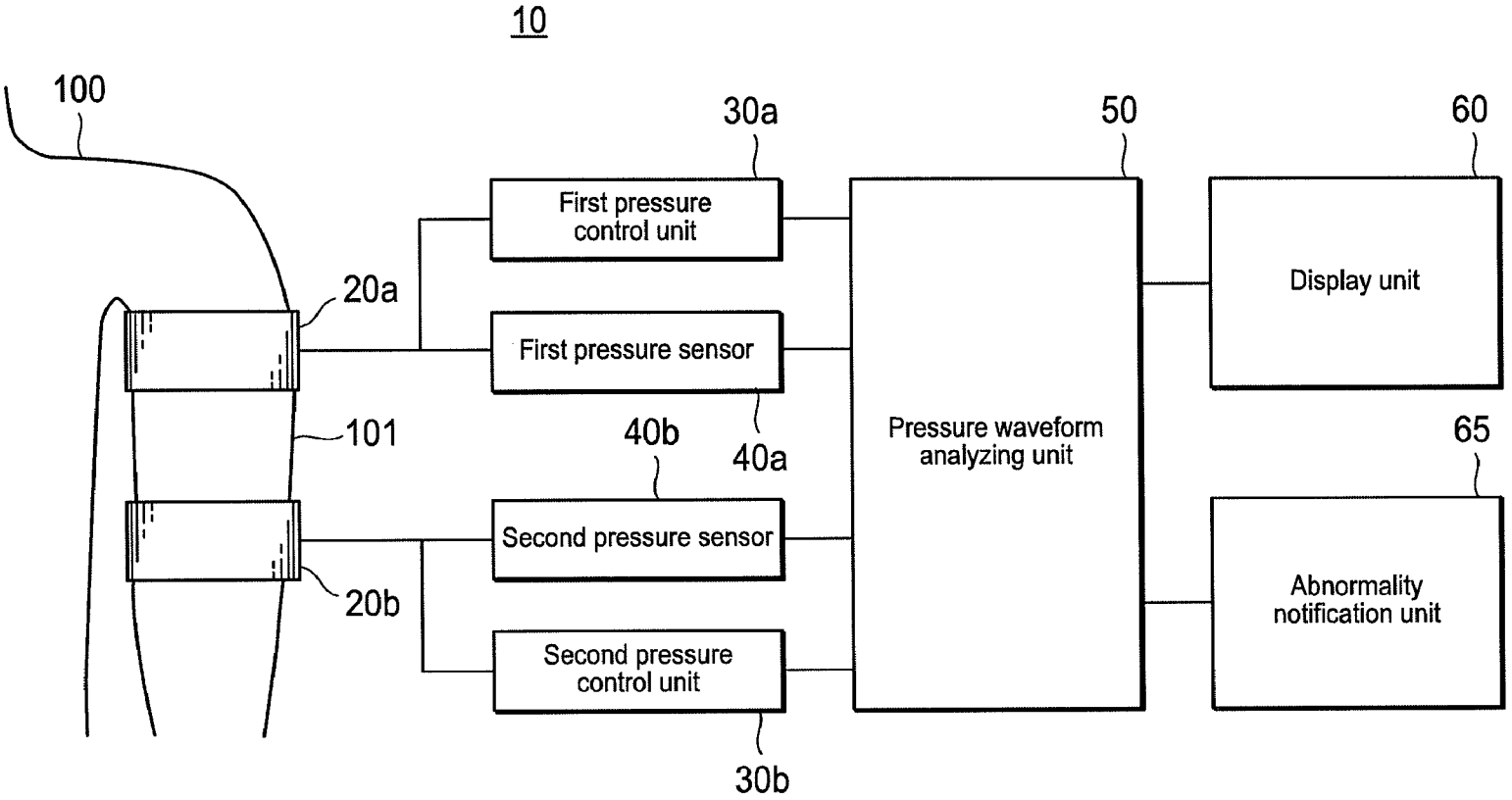
FIG. 1 is a block diagram showing a venous pressure measurement apparatus.

FIG. 1 is a block diagram showing a venous pressure measurement apparatus 10 according to an embodiment. Referring to FIG. 1, a living body 100 is illustrated along with the venous pressure measurement apparatus 10, and a first cuff 20a and a second cuff 20b are attached to an upper arm 101 of the living body 100.

In order to measure the mean venous pressure, the venous pressure measurement apparatus 10 includes the first cuff 20a (first pulse wave sensor), the second cuff 20b (second pulse wave sensor), a first pressure control unit (pressure control unit) 30a, a second pressure control unit (pressure control unit) 30b, a first pressure sensor 40a (first pulse wave sensor), a second pressure sensor 40b (second pulse wave sensor), a pressure waveform analyzing unit (analyzing unit, venous pressure calculation unit) 50, a display unit 60, and an abnormality notification unit 65. As disclosed below in further detail, the pressure waveform analyzing unit 50 is a device which receives pulse waves from the first and second cuffs respectively as electric signals. Accordingly, it will be understood by those skilled in the art that the pressure waveform analyzing unit 50 will comprise an electric circuit. As also explained below, the pressure waveform analyzing unit 50 will (2) receive pressure values (data) from the first and second pressure control units 30a, 30b, (3) analyze a correlation between the pulse waves from the first and second cuffs 20a, 20b, (4) perform calculations to determine venous pressure, and (5) transmit waveforms and various calculation results to a display unit 60 (e.g., a liquid crystal display). As is known, an electronic device that receives data and pulse waves as electric signals, uses such information to analyze correlation between two pulse waves, performs calculations, and transmits waveforms and calculation results to an electronic display unit, is commonly referred by those skilled in the art as a computer, a processor or an electronic processor circuit.

The first cuff 20a is attached by being wound around the upper arm 101 in the vicinity of the axillary region which is a part of the living body (first portion). An attached portion is pressurized under control of the first pressure control unit 30a, and a pulse wave (hereinafter, referred to as a "first pulse wave") which is a vibration of the vascular wall detected as a pressure received from the pressurized portion is transmitted to the first pressure sensor 40a. In addition, the position where the first cuff 20a is attached is not particularly limited if both an artery and a vein exist there. The first pulse wave may include pulse waves of the artery and the vein.

The second cuff 20b has a function similar to the first cuff 20a. The second cuff 20b is attached to a portion (second portion) distal to the first cuff 20a with respect to the heart in the upper arm 101. The second cuff 20b pressurizes the attached portion under control of the second pressure control unit 30b and transmits a pulse wave (hereinafter, referred to as a "second pulse wave") received from the pressurized portion to the second pressure sensor 40b. The position where the second cuff 20b is attached is not particularly limited if it is different from the attached portion of the first cuff 20a. However, the second cuff 20b is attached to the position where at least the pulse wave of the artery can be detected. Therefore, the second pulse wave includes at least the arterial pulse wave.

According to an embodiment, the pressure applied by the first cuff 20a to the living body when the correlation between the first pulse wave and the second pulse waves is minimized is estimated as the mean venous pressure based on a principle of the oscillometric method. Such estimation can be made based on a fact that (1) the applied pressure by the cuff when the venous pulse wave is maximized can be estimated as the mean venous pressure since the venous pulse wave is maximized when a pressure difference between the inside and the outside of the venous blood vessel is minimized, and (2) the correlation between pulse waves in the distal and proximal locations is reduced as the venous pulse wave component increases since the venous pulse wave is decreased as the venous blood vessel becomes distal with respect to the heart with its high compliance.

If a pressure higher than the mean venous pressure is applied to the vein, the venous pulse component gradually decreases as the applied pressure increases. If the vein is perfectly occluded, the venous pulse component is disappeared from the pulse wave. The venous pulse component of the pulse wave decreases even when a pressure smaller than the mean venous pressure is applied to the vein.

Here, a backflow valve exists in the venous intravascular lumen of the extremity. The venous pulse is more strongly exhibited in the vein of the upper arm in the vicinity of the axillary region proximal to the backflow valve in comparison with the vein distal to the backflow valve with respect to the heart. Therefore, it is possible to increase a difference of the venous component between the first pulse wave and the second pulse wave by attaching the first cuff 20a and the second cuff 20b over the backflow valve and attaching the first cuff 20a as near as possible to the heart. As a result, it is possible to more accurately measure the correlation between the first pulse wave and the second pulse wave and improve the measurement accuracy of the mean venous pressure. Such a condition can be satisfied by attaching the first cuff 20a in the upper arm 101 in the vicinity of the axillary region and attaching the second cuff 20b in the portion distal to the first cuff 20a with respect to the heart in the upper arm 101.

Since the mean venous pressure measured when the first cuff 20a has the same height as that of the heart can be considered as the central venous pressure, the central venous pressure can be measured in such a body position by using the venous pressure measurement apparatus according to the present embodiment.

The first pressure control unit 30a controls the first cuff 20a so that the portion where the first cuff 20a is attached is pressurized with a predetermined pressure, and the applied pressure is changed. The first pressure control unit 30a may pressurize the portion where the first cuff 20a is attached, for example, by sending air to the first cuff 20a.

The second pressure control unit 30b may control the second cuff 20b so that the portion where the second cuff 20b is attached is pressurized with a predetermined pressure, and the applied pressure can be changed. The second pressure control unit 30b may pressurize the portion where the second cuff 20b is attached, for example, by sending air to the second cuff 20b.

The first pressure sensor 40a receives the first pulse wave transmitted from the first cuff 20a and outputs it to the pressure waveform analyzing unit 50 as an electric signal. The first pulse wave received by the first pressure sensor 40a from the first cuff 20a is a pressure waveform obtained by using air as a medium. The first pressure sensor 40a may be a piezoelectric element for converting the pressure signal into the electric signal.

The second pressure sensor 40b receives the second pulse wave transmitted from the second cuff 20b and outputs it to the pressure waveform analyzing unit 50 as an electric signal. The second pulse wave received by the second pressure sensor 40b from the second cuff 20b is a pressure waveform obtained by using air as a medium. The second pressure sensor 40b may be a piezoelectric element for converting the pressure signal into the electric signal.

The pressure waveform analyzing unit 50 receives the first pulse wave and second pulse wave from the first pressure sensor 40a and the second pressure sensor 40b, respectively, and receives the pressure values applied to the upper arm from each of the first pressure control unit 30a and the second pressure control unit 30b, and calculates the venous pressure based on the pressure applied to the living body by the first cuff 20a when the correlation between the first pulse wave and the second pulse waves is minimized The pressure waveform analyzing unit 50 transmits the waveforms of the first pulse wave or the second pulse wave and various calculation results to the display unit 60.

The display unit 60 displays various waveforms or various calculation results received from the pressure waveform analyzing unit 50. The display unit 60 may include, for example, a liquid crystal display. In addition, the display unit 60 may be a touch panel which receives a signal for switching display from the outside.

The abnormality notification unit 65 determines whether the venous pressure calculated by the pressure waveform analyzing unit 50 exceeds a threshold value. If it is determined that the venous pressure exceeds the threshold value, this fact is notified. Such a notification to a user may be made by displaying, on a display unit 60, an indication for indicating abnormality along with the measured venous pressure value, or by transmitting a notification for abnormality along with the measured venous pressure value to other devices.

The threshold value may be set to a general numerical value used when a surgeon determines the abnormality in clinical practice.

Figure 2:
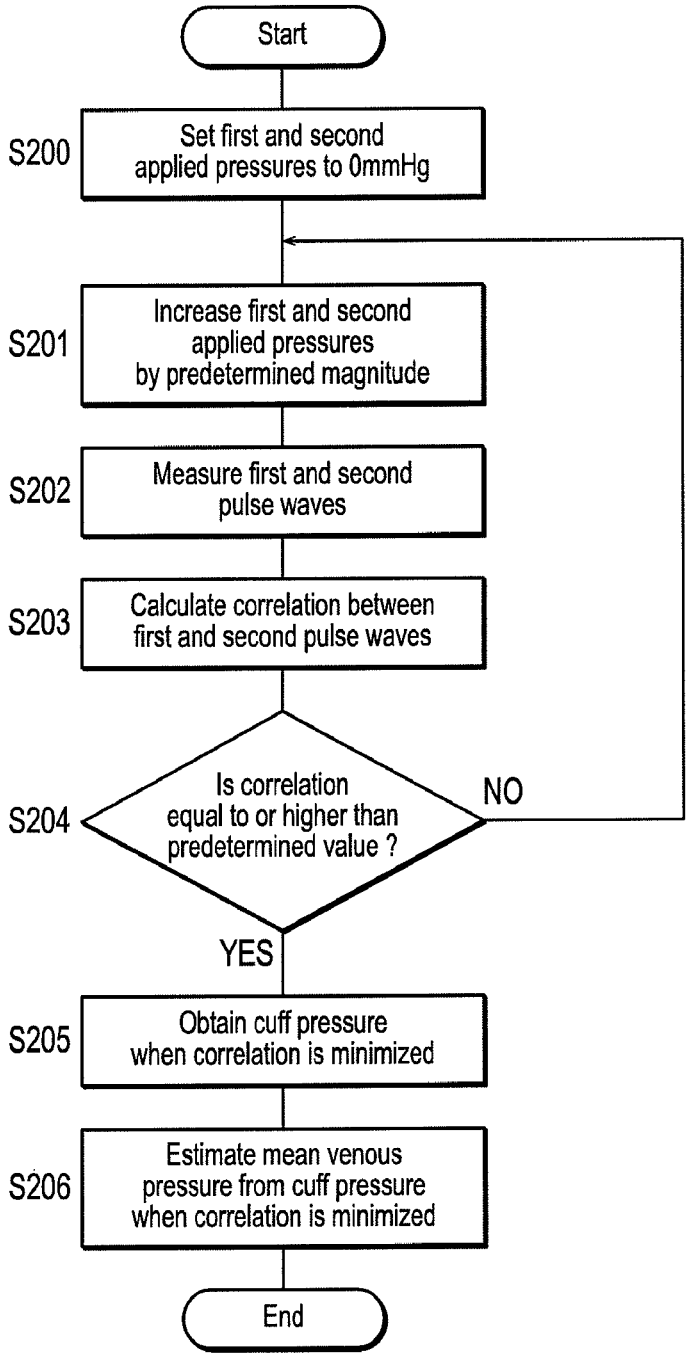
FIG. 2 is a flowchart showing a process of measuring a mean venous pressure by the venous pressure measurement apparatus.

FIG. 2 is a flowchart showing a process of measuring the mean venous pressure by the venous pressure measurement apparatus according to an embodiment.

The first pressure control unit 30a and the second pressure control unit 30b set, to 0 mmHg (S200), the pressure (hereinafter, referred to as a "first applied pressure") applied to the upper arm 101 in the vicinity of the axillary region by the first cuff 20a attached to the proximal location and the pressure (hereinafter, referred to as a "second applied pressure") applied to the upper arm 101 by the second cuff 20b attached to the distal location with respect to the heart.

The first pressure control unit 30a and the second pressure control unit 30b increase the first applied pressure and the second applied pressure, respectively, by a predetermined magnitude (S201). Here, the predetermined magnitude as a pressure increment may be set, for example, to 10 mmHg. Although the magnitudes of the first applied pressure and the second applied pressure are set to the same value according to the present embodiment, different values may be set.

The first pulse wave is measured by using the first cuff 20a and the first pressure sensor 40a, and the second pulse wave is measured by using the second cuff 20b and the second pressure sensor 40b at the same time (S202). The pressure waveform analyzing unit 50 calculates the correlation between the first pulse wave and the second pulse wave (S203).

Figure 3:
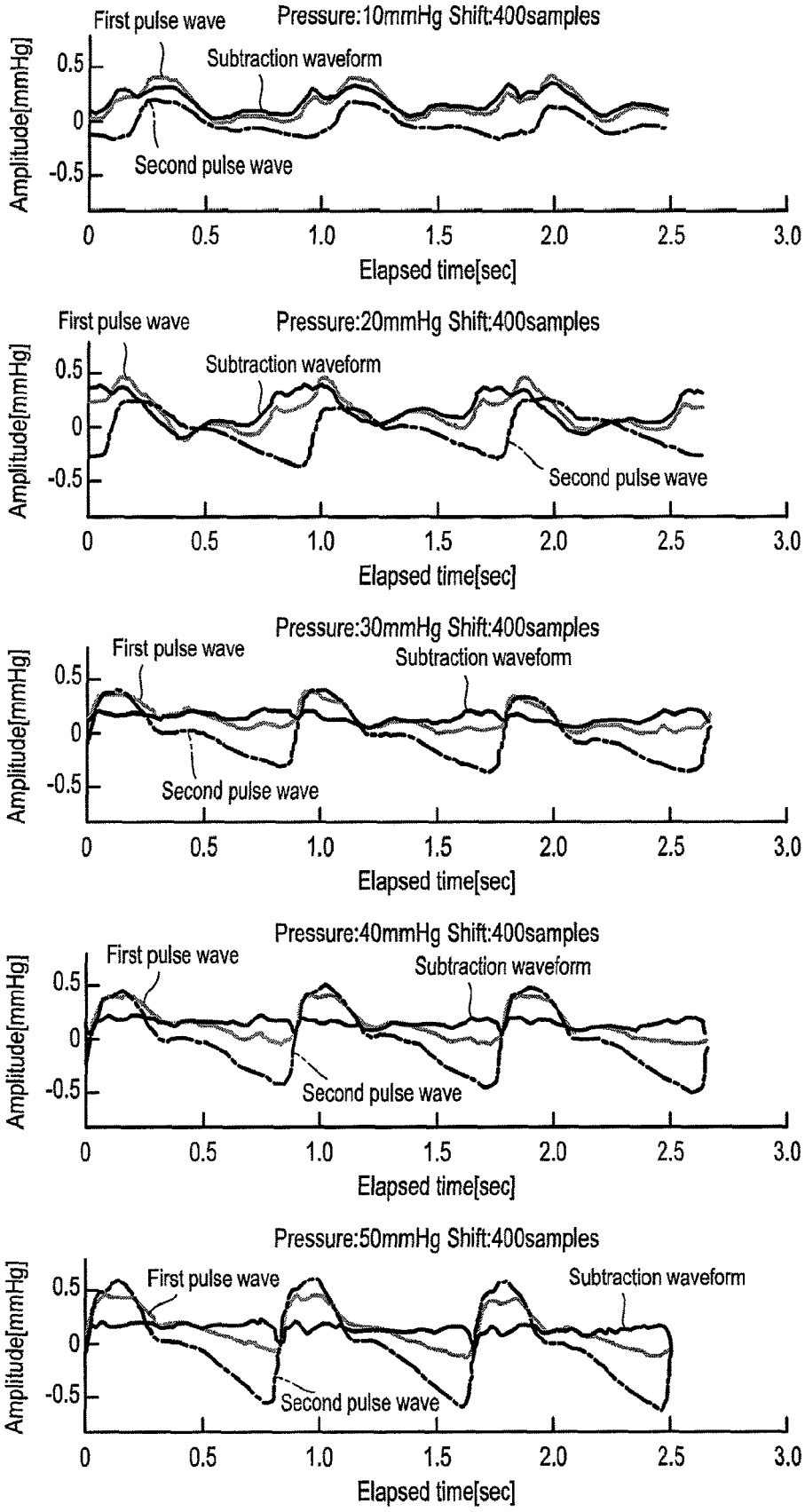
FIG. 3 shows graphs of pulse waves in the proximal and distal locations with respect to the heart in the upper arm and subtraction waveforms thereof.

FIG. 3 shows graphs of pulse waves in the proximal and distal locations with respect to the heart in the upper arm and subtraction waveforms thereof. Here, the abscissa axis denotes the elapsed time, and the ordinate axis denotes the amplitude of the pulse wave. In addition, the amplitude is indicated as a value obtained by subtracting the central value (DC component) from each pulse wave.

FIG. 3 shows the first pulse wave (proximal pulse wave) and the second pulse wave (distal pulse wave) obtained when the first applied pressure and the second applied pressure are changed from 10 mmHg to 50 mmHg, and waveforms obtained by subtracting a correlation component of the second pulse wave from the first pulse wave on a 10 mmHg basis.

The correlation between the first pulse wave and the second pulse wave can be calculated by obtaining the subtraction waveform by subtracting the second pulse wave in the distal location of the upper arm from the first pulse wave in the proximal location of the upper arm with respect to the heart. If the amplitude of the subtraction waveform increases, the correlation decreases. If the amplitude decreases, the correlation increases. Here, in the graphs of FIG. 3, phase correction for matching the phases between the first pulse wave and the second pulse wave is made considering the time during the pressure pulse wave propagates from the first cuff 20a to second cuff 20b. Concretely, the time taken for transmitting the pressure pulse wave from the first cuff 20a to the second cuff 20b is set to 40 msec, and the sample data on a 0.1 msec basis is shifted by a length of 400 samples relatively. In addition, the phase correction may be made by measuring the temporal difference between peaks of the first pulse wave and that of the second pulse wave or peaks of differentiated waveforms and removing such a temporal difference. Furthermore, the correlation between the first pulse wave and the second pulse wave as the applied pressure increases is obtained, and the shift amount having the maximum correlation may be set to the shift amount for the phase correction.

Figure 4:
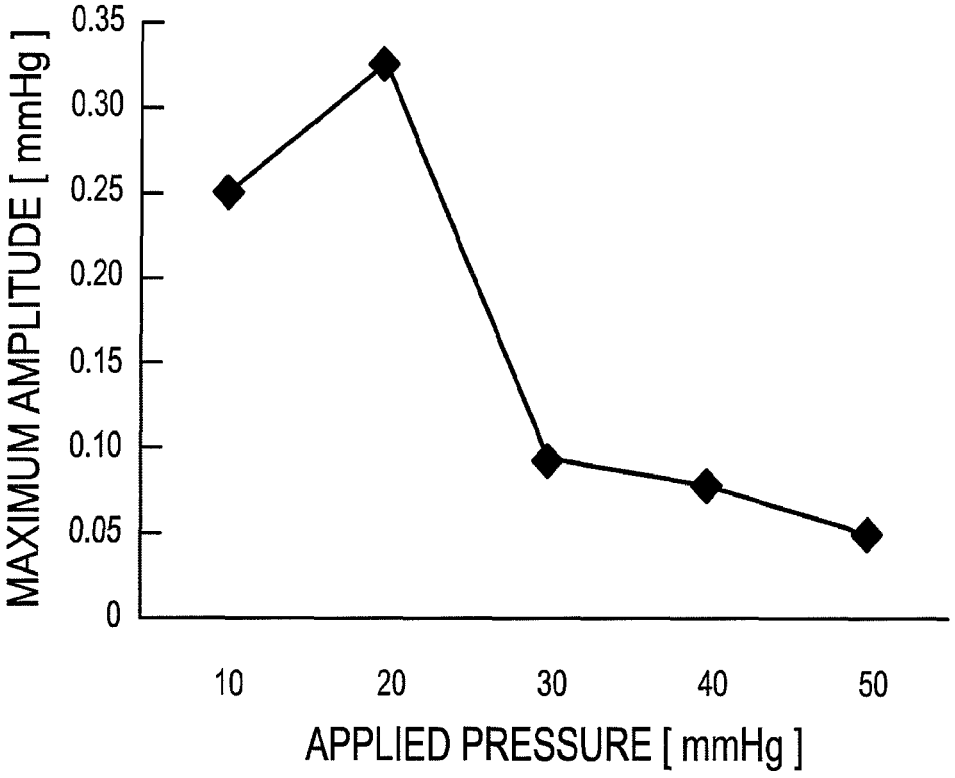
FIG. 4 is a diagram showing a relation between applied pressure and the maximum amplitude of the subtraction waveform.

FIG. 4 is a diagram showing a relation between the applied pressure and the maximum amplitude of the subtraction waveform.

Since the amplitude of the subtraction waveform is maximized when the first applied pressure and the second applied pressure are set to 20 mmHg, the mean venous pressure may be estimated as 20 mmHg.

It goes without saying that the measurement accuracy can be improved by correcting the mean venous pressure estimated in this manner as necessary. For example, general data regarding a relation between the cuff pressure and intravascular pressure measured using a catheter may be prepared in advance. The correction may be made by setting the intravascular pressure obtained through comparison with the first applied pressure (cuff pressure) when the amplitude of the subtraction waveform is maximized to the mean venous pressure.

Figure 5:
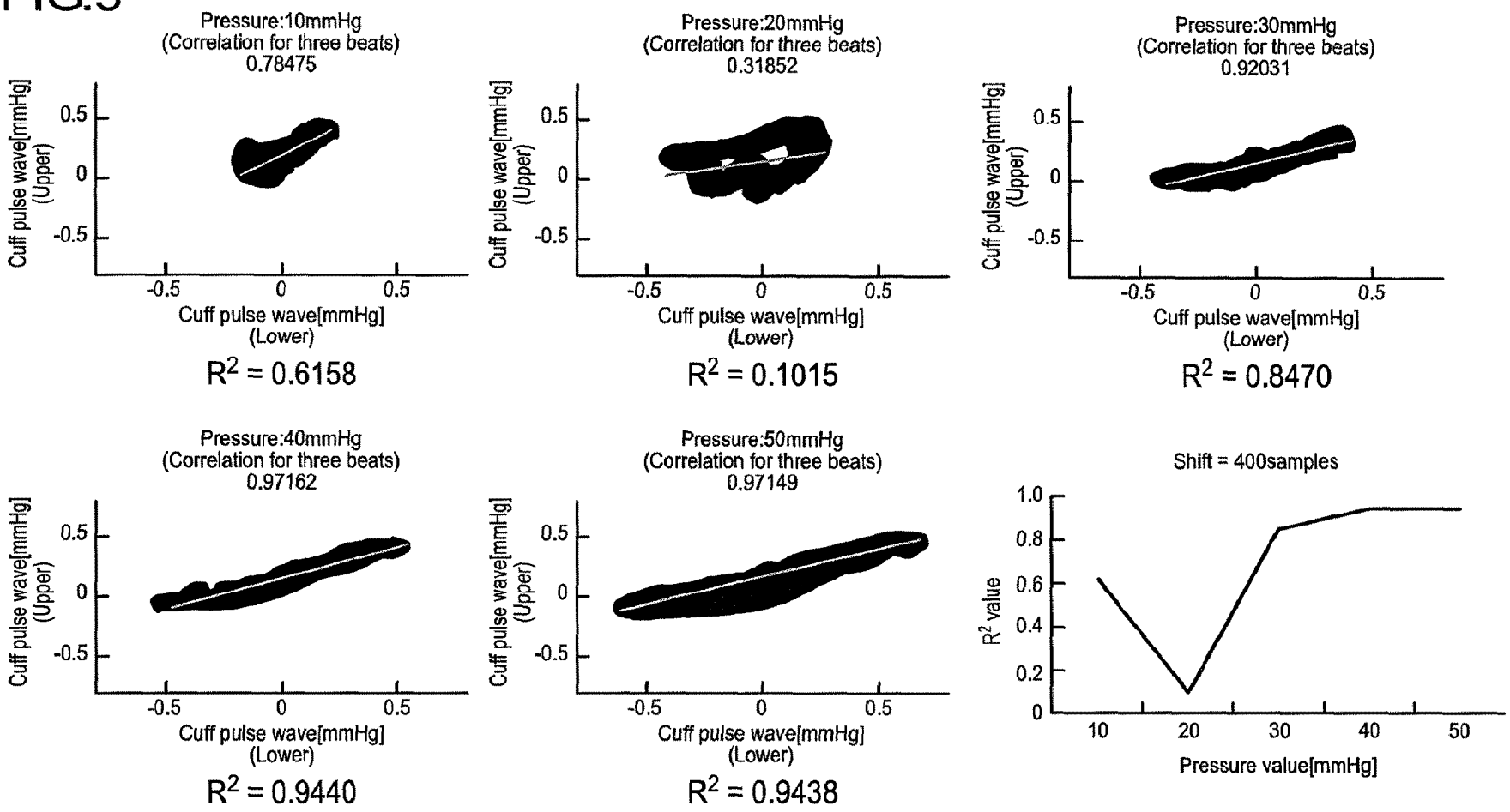
FIG. 5 shows graphs of a relation between first pulse wave and second pulse wave on a first applied pressure value basis.

FIG. 5 shows graphs indicating a relation between the first pulse wave and the second pulse wave on the first applied pressure value basis. The abscissa axis denotes the amplitude of the second pulse wave, and the ordinate axis denotes the amplitude of the first pulse wave. In FIG. 5, the contribution ratio $R^2$ indicating the correlation between the first pulse wave and the second pulse wave is showed together. The value $R^2$ increases as the correlation between the first pulse wave and the second pulse wave increases.

The value $R^2$ is minimized when the first applied pressure is at 20 mmHg. Therefore, it is apparent that the correlation between the first pulse wave and the second pulse wave is the lowest at this condition.

The venous pressure measurement apparatus 10 increases the first applied pressure and the second applied pressure (S201), measures the first pulse wave and the second pulse wave (S202), and calculates the correlation between the first pulse wave and the second pulse wave (S203) in an iterative manner until the value $R^2$ indicating the correlation between the first pulse wave and the second pulse wave is equal to or higher than a predetermined value (NO at S204). The aforementioned predetermined value may be set to 0.9, for example.

If the value $R^2$ is equal to or higher than the predetermined value (YES at S204), the pressure waveform analyzing unit 50 obtains the first applied pressure when the value $R^2$ is minimized based on the previous measurement result (S205). The pressure waveform analyzing unit 50 estimates the obtained first applied pressure as the mean venous pressure (S206).

Also, the measurement of the first pulse wave and the second pulse wave may be terminated at the time when the value $R^2$ which is indicates the correlation between the first pulse wave and second pulse wave calculated in step S203 is changed from a decrease to an increase, and the first applied pressure when the value $R^2$ is minimized until that time may be estimated as the mean venous pressure.

The venous pressure measurement apparatus in an embodiment measures the mean venous pressure by estimating that the cuff pressure when the correlation between pulse waves in the proximal and distal locations with respect to the heart is minimized is the mean venous pressure. This is equivalent to the case where the venous pulse wave component is extracted from the proximal pulse wave with reference to the distal pulse wave with respect to the heart, and the cuff pressure when the venous pulse wave component is maximized is estimated as the mean venous pressure.

The venous pressure measurement apparatus in an embodiment also estimates the venous pressure by using the venous pulse wave caused by systole and diastole of the right atrium. Therefore, since pressure propagation of the venous pulse wave from the heart is not hindered even if congestion occurs due to occlusion of the vein, existence or non-existence of the congestion does not matter in the measurement.

Using an embodiment of the venous pressure measurement apparatus, by extracting the venous pulse wave and using the change of it, it is possible to measure the venous pressure using simple instruments while the living body is under natural condition.

The venous pressure measurement apparatus in another embodiment will now be described. However, overlapping description with the embodiments already described will not be repeated.

An embodiment is different from others in that the applied pressure when the correlation between the first pulse wave which is a pulse wave in the proximal location with respect to the heart and the second pulse wave which is a pulse wave in the distal location is minimized is estimated as the mean venous pressure in the first embodiment, whereas the applied pressure when the amplitude of the first pulse wave after subtracting the arterial pulse wave component from the first pulse wave is maximized is estimated as the mean venous pressure in the present embodiment.

Figure 6:
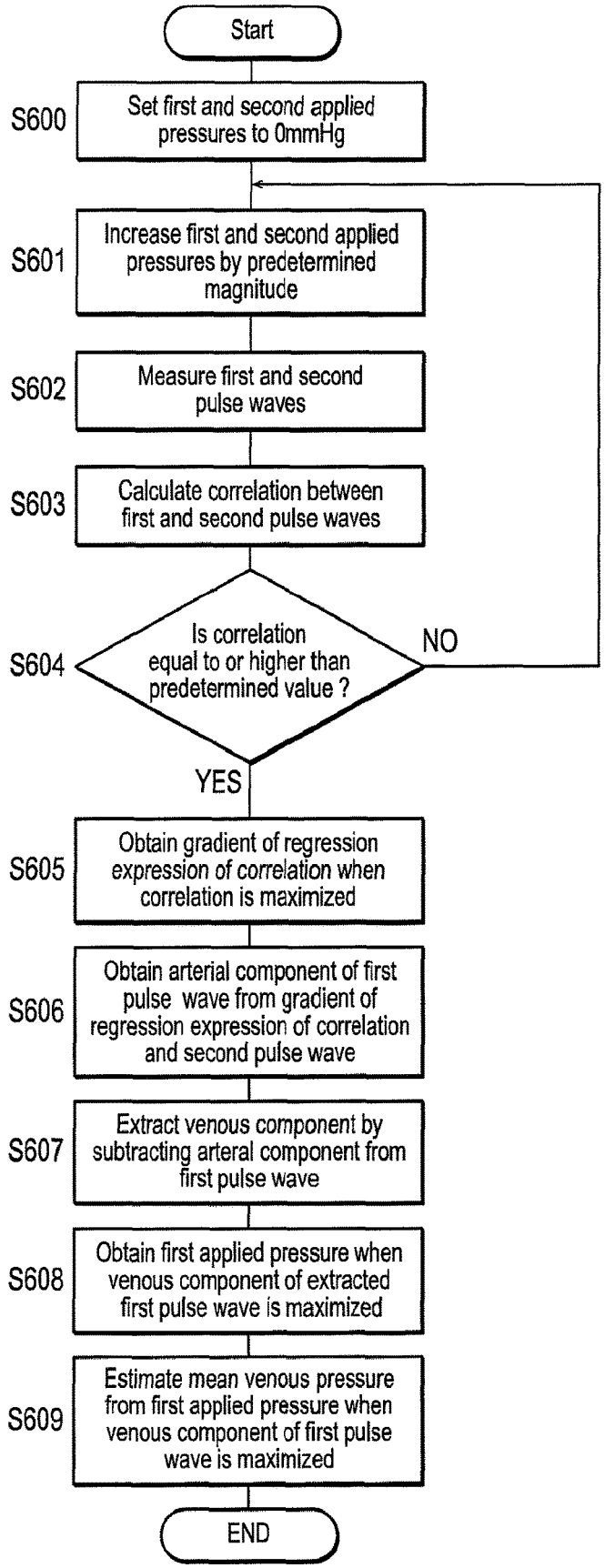
FIG. 6 is a flowchart showing a process of measuring a mean venous pressure by the venous pressure measurement apparatus.

FIG. 6 is a flowchart showing a process of measuring the mean venous pressure by the venous pressure measurement apparatus.

Similar to the previous process description given in FIG. 2, in steps S600 to S604, the measurement of the first pulse wave and the second pulse wave is repeated until the value $R^2$ indicating the correlation between them is equal to or higher than a predetermined value.

The pressure waveform analyzing unit 50 calculates a slope of the regression expression of the correlation between the first pulse wave and the second pulse wave when the value $R^2$ is maximized (S605).

The regression expression is a formula expressing the straight line in the graph of the relation between the first pulse wave and the second pulse wave along with the measurement results in FIG. 5. Referring to FIG. 5, the value $R^2$ is maximized when the first applied pressure is 40 mmHg. The pressure waveform analyzing unit 50 calculates the slope S of the regression expression at this condition.

The pressure waveform analyzing unit 50 obtains the arterial pulse wave component of the first pulse wave by multiplying the second pulse wave by the slope S of the regression expression calculated in step S605 assuming that the arterial component ratio between the first pulse wave and the second pulse wave is constant (S606). Here, the arterial pulse wave component means a part of the pulse waves, caused by the arterial pulsation.

The pressure waveform analyzing unit 50 extracts the venous pulse wave component of each first pulse wave by subtracting the arterial pulse wave component of the first pulse wave obtained in step S606 from each first pulse wave (S607). Here, the venous pulse wave component means a part of the pulse waves, caused by the venous pulsation.

The pressure waveform analyzing unit 50 obtains the first applied pressure when the amplitude of the venous pulse wave components of each first pulse wave extracted in step S607 is maximized (S608) and estimates the obtained first applied pressure as the mean venous pressure (S609).

In the venous pressure measurement apparatus according to an embodiment, by extracting the venous pulse wave and using the change of it, it is possible to measure the venous pressure using simple instruments while the living body is under natural condition.

The venous pressure measurement apparatus according to another embodiment will now be described.

Figure 7:
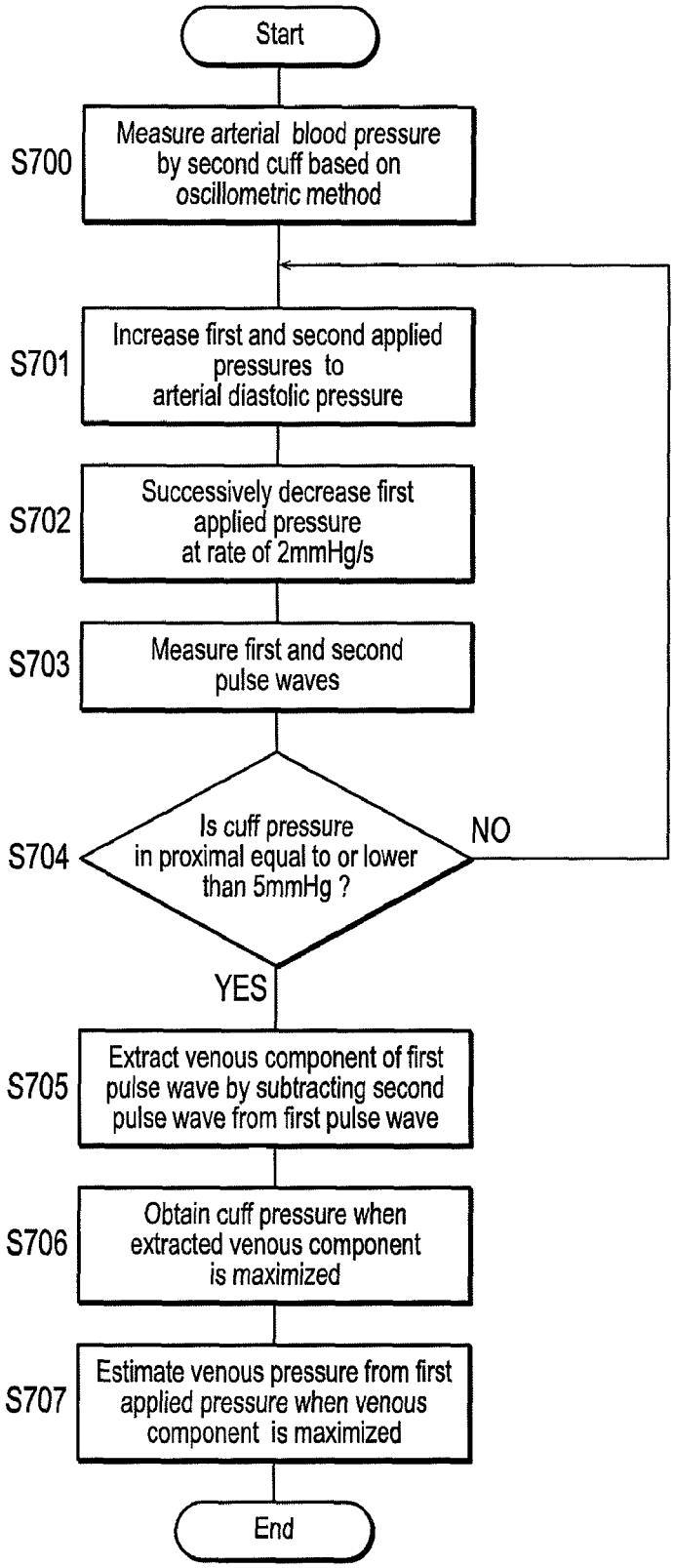
FIG. 7 is a flowchart showing a process of measuring a mean venous pressure by the venous pressure measurement apparatus.

FIG. 7 is a flowchart showing a process of measuring the mean venous pressure by the venous pressure measurement apparatus according to an embodiment.

The arterial blood pressure is measured based on an oscillometric method using the second cuff 20b and the second pressure control unit 30b (S700). Then, the first applied pressure applied to the living body by the first cuff 20a and the second applied pressure applied to the living body by the second cuff 20b are increased to the arterial diastolic pressure (S701). Then, the first applied pressure applied by the first cuff 20a is successively decreased at a rate of 2 mmHg/s while the second applied pressure is maintained at the arterial diastolic pressure (S702), and the first pulse wave and the second pulse wave are measured respectively (S703). The measurement is continued until the first applied pressure is decreased to be equal to or lower than 5 mmHg (NO at S704).

If the first applied pressure is equal to or lower than 5 mmHg (YES at S704), the venous pulse wave component is extracted from the first pulse wave by subtracting the correlation component of a series of second pulse waves from a series of first pulse waves (S705). Then, the first applied pressure when the amplitude of the venous component of the extracted first pulse wave is maximized is obtained (S706). The obtained first applied pressure is estimated as the mean venous pressure (S707).

According to an embodiment, the venous pulse wave component is removed from the second pulse wave by pressed closing the vein in a portion where the second cuff 20b is installed while the second applied pressure is maintained at the arterial diastolic blood pressure which is higher than the mean venous pressure. In addition, the venous pulse wave component is extracted from the first pulse wave by subtracting the arterial pulse wave component extracted from the second pulse wave from the first pulse wave, and the first applied pressure when the amplitude of the extracted venous pulse wave component is maximized is estimated as the mean venous pressure.

In the venous pressure measurement apparatus according to an embodiment, by extracting the venous pulse wave and using the change of it, it is possible to measure the venous pressure using simple instruments while the living body is under natural condition.

Figure 8:
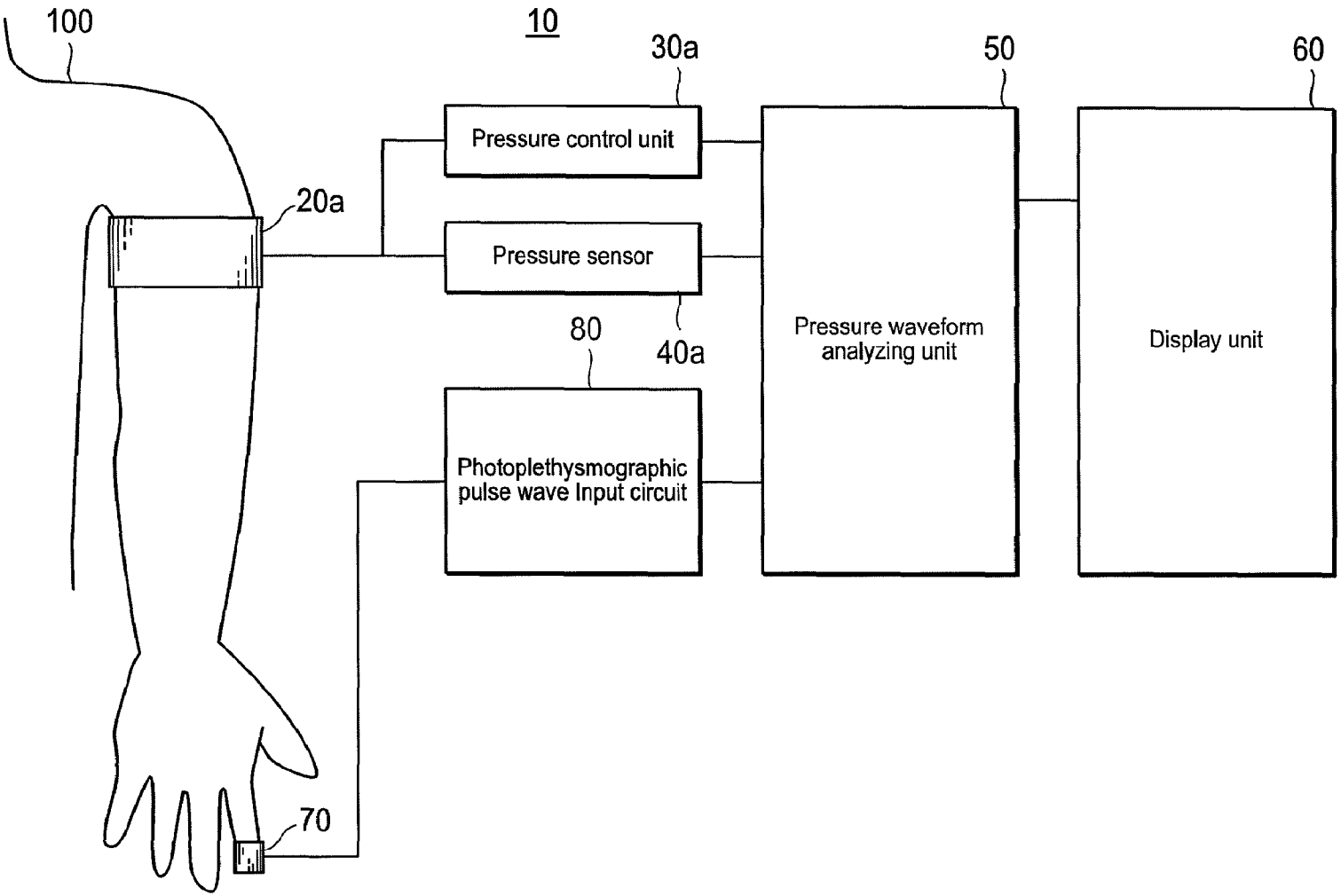
FIG. 8 is a block diagram showing a venous pressure measurement apparatus.

FIG. 8 is a block diagram showing the venous pressure measurement apparatus 10 according to another. In FIG. 8, the living body 100 is shown along with the venous pressure measurement apparatus 10, in which the first cuff 20a is attached to the axillary region of the living body 100, and the photoplethysmographic pulse wave sensor 70 is attached in the fingertip.

According to an embodiment, the photoplethysmographic pulse wave sensor 70 and the photoplethysmographic pulse wave input circuit 80 are used instead of the second cuff 20b and the second pressure sensor 40b of the first embodiment or the third embodiment. That is, the second pulse wave in the first embodiment and the third embodiment is detected by the photoplethysmographic pulse wave sensor 70 and the photoplethysmographic pulse wave input circuit 80. Other parts are similar to the first embodiment or the third embodiment, so overlapping description will not be repeated.

The photoplethysmographic pulse wave sensor 70 includes a light emitting element that emits light of a wavelength band absorbed by the hemoglobin and a light receiving element that receives light emitted from the light emitting element. The photoplethysmographic pulse wave sensor 70 is attached to the fingertip of the living body to detect the photoplethysmographic pulse wave. The photoplethysmographic pulse wave sensor 70 is attached to the distal location to the first cuff 20a with respect to the heart. As a result, it is possible to detect the second pulse wave having a higher percentage of the arterial pulse wave components in comparison with the first pulse wave.

The photoplethysmographic pulse wave input circuit 80 receives the electric signal of the photoplethysmographic pulse wave from the photoplethysmographic pulse wave sensor 70, amplifies it to be an appropriate voltage, and outputs it to the pressure waveform analyzing unit 50.

Similar to the first embodiment to the third embodiment, in the venous pressure measurement apparatus according to the present embodiment, by extracting the venous pulse wave and using the change of it, it is possible to measure the venous pressure using simple instruments while the living body is under natural condition.

Figure 9:
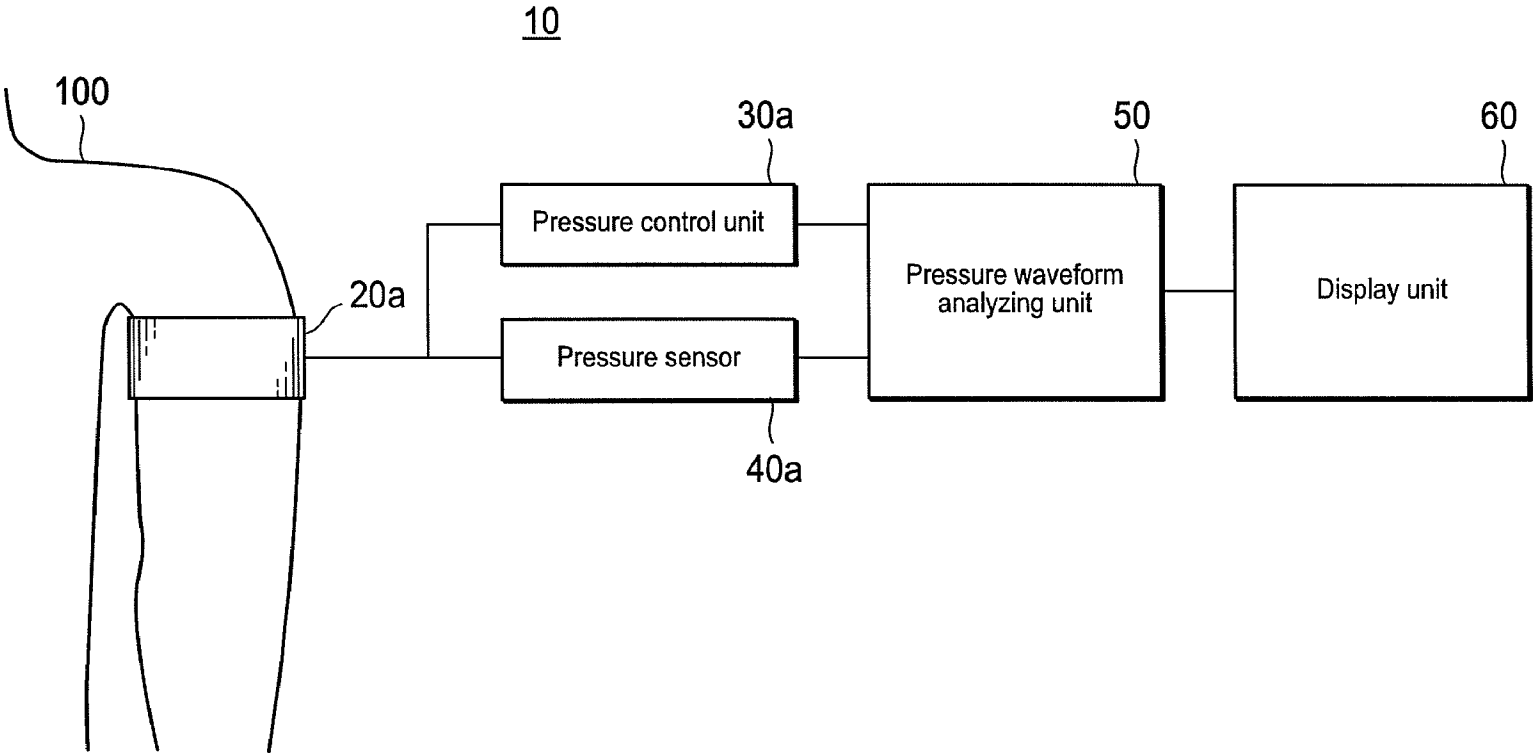
FIG. 9 is a block diagram showing a venous pressure measurement apparatus.

FIG. 9 is a block diagram showing the venous pressure measurement apparatus 10 according to another embodiment.

As shown in FIG. 9, the venous pressure measurement apparatus 10 includes the first cuff 20a, the first pressure control unit 30a, the first pressure sensor 40a, the pressure waveform analyzing unit 50, and the display unit 60. That is, the first embodiment to the third embodiment included two cuffs, two pressure control units, and two pressure sensors. However, the venous pressure measurement apparatus 10 according to the present invention includes a single cuff, a single pressure control unit, and a single pressure sensor. Other configurations of the venous pressure measurement apparatus 10 are similar to those of the first embodiment, so overlapping description will not be repeated.

Figure 10:
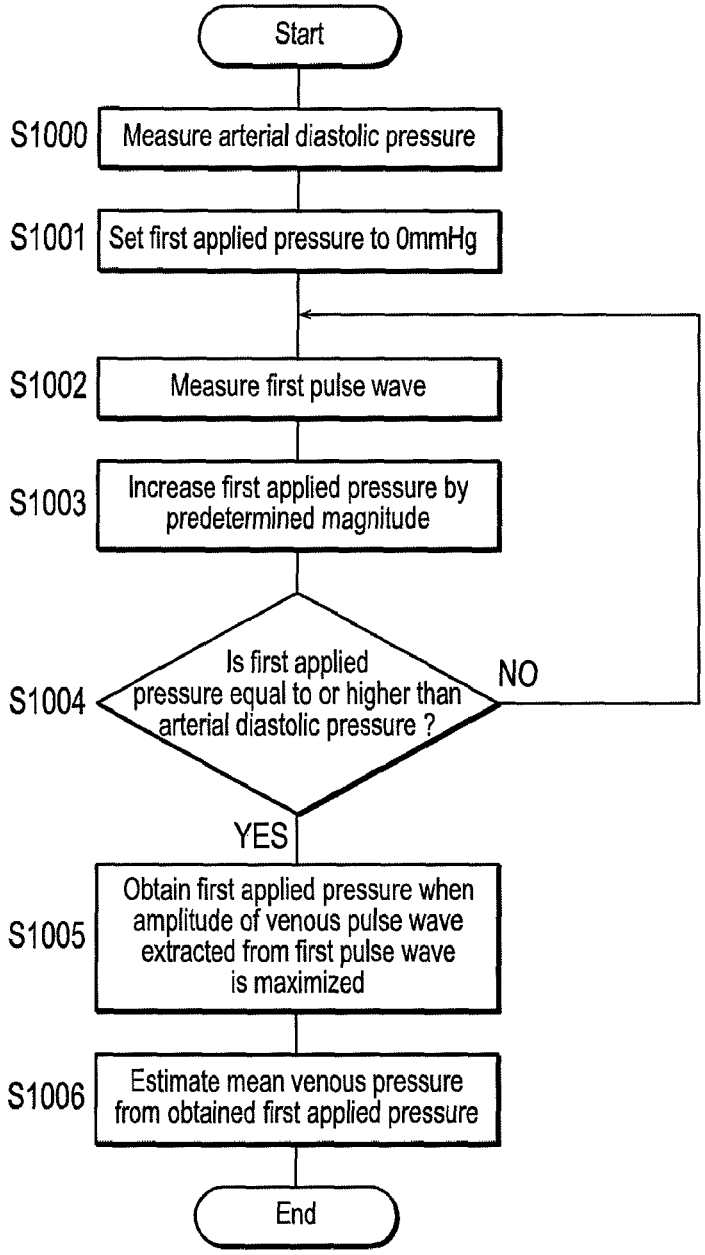
FIG. 10 is a flowchart showing a process of measuring a mean venous pressure by the venous pressure measurement.

FIG. 10 is a flowchart showing a process of measuring the mean venous pressure by the venous pressure measurement apparatus according to the present embodiment.

The arterial diastolic pressure is measured by using the first cuff 20a and the first pressure sensor 40a (S1000). The arterial diastolic pressure can be measured based on a typical oscillometric method.

Then, the first cuff 20a is attached to the upper arm in the vicinity of the axillary region, and the first applied pressure applied to the upper arm in the vicinity of the axillary region by the first cuff 20a is set to 0 mmHg using the pressure control unit 30a (S1001). Then, the first pulse wave is measured by the first cuff 20a and the first pressure sensor 40a, and the first applied pressure is increased by a predetermined increment (S1004). In this manner, the measurement of the first pulse wave done by increasing the first applied pressure is repeated until the first applied pressure reaches the arterial diastolic pressure measured in step S1000 (NO in S1004).

When the first applied pressure is equal to or higher than the arterial diastolic pressure (YES at S1004), the measurement is terminated, so that the pulse wave detected by maximizing the first applied pressure is set to a reference pulse wave, the venous pulse wave component is extracted from the first pulse wave by subtracting the arterial pulse wave component extracted from the reference pulse wave from the first pulse wave, the first applied pressure when the amplitude of the venous pulse wave extracted is maximized is obtained (S1005), and the first applied pressure obtained is estimated as the mean venous pressure (S1006).

According to an embodiment, the cuff pressure within a range equal to or lower than the arterial diastolic pressure is applied to the upper arm in the vicinity of the axillary region, and the cuff pressure when the amplitude of the pulse wave detected by using the cuff is maximized is obtained by changing the cuff pressure. That is, the mean venous pressure is estimated by detecting the change of the amplitude of the pulse pressure caused by pressing and closing the vein when the cuff pressure reaches the mean venous pressure.

In the venous pressure measurement apparatus according to an embodiment, by using the change of the venous pulse wave, it is possible to measure the venous pressure using simple instruments while the living body is under natural condition.

The venous pressure measurement apparatus according to another embodiment will be described.

This embodiment is different from the prior described embodiment in that the first applied pressure when the amplitude of the pulse wave is maximized by changing the first applied pressure is estimated as the mean venous pressure according to the fifth embodiment, whereas the pulse wave detected by maximizing the first applied pressure is set to a reference pulse wave, and the first applied pressure when the correlation between the reference pulse wave and the pulse wave is minimized is estimated as the mean venous pressure according to the sixth embodiment. Other parts of the present embodiment are similar to the fifth embodiment, so overlapping description will not be repeated.

Figure 11:
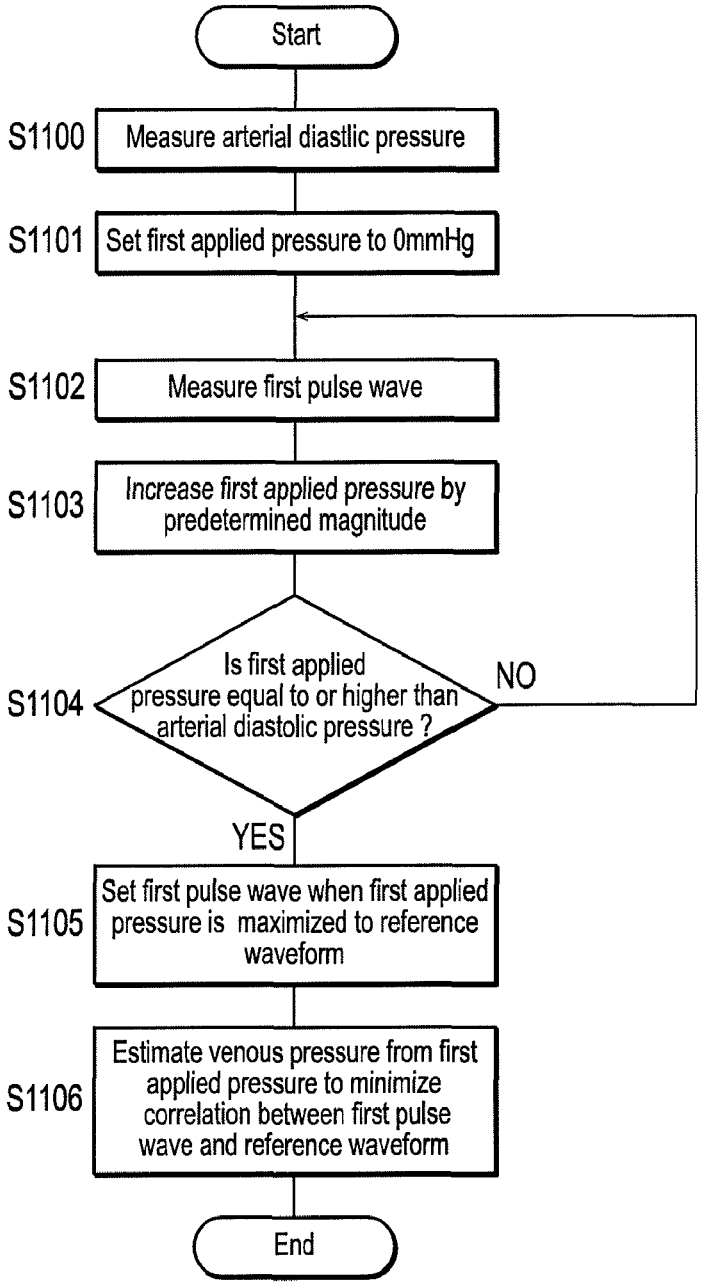
FIG. 11 is a flowchart showing a process of measuring a mean venous pressure by the venous pressure measurement apparatus.

FIG. 11 is a flowchart showing a process of measuring the mean venous pressure by the venous pressure measurement apparatus according to an embodiment.

Similar to steps S1000 to S1004 of the fifth embodiment, in steps S1100 to S1104, the first pulse wave is measured by increasing the first applied pressure from 0 mmHg with a predetermined increment within a range equal to or lower than the arterial diastolic pressure.

The pressure waveform analyzing unit 50 stores the data of the measured first pulse wave along with the first applied pressure.

Then, the first pulse wave when the first applied pressure is increased to the arterial diastolic pressure as the maximum value is set to a reference waveform (S1105), and the first applied pressure when the correlation between the reference waveform and the pulse wave is minimized is estimated as the mean venous pressure (S1106). The correlation may be obtained as in the first embodiment.

Here, in order to synchronize the first pulse wave with the reference pulse wave, any one of the electrocardiogram and the photoplethysmographic pulse wave may be used.

In the venous pressure measurement apparatus according to the present embodiment, by extracting the venous pulse wave and using the change of it, it is possible to measure the venous pressure using simple instruments while the living body is under natural condition.

Although the venous pressure measurement apparatus according to the embodiments of the invention have been described hereinbefore, this invention is not limited to above-mentioned embodiments.

For example, although the pulse wave is measured by increasing the applied pressure from 0 mmHg in all of the embodiments excluding the third embodiment, the pulse wave may be measured by decreasing the applied pressure from an appropriate pressure. In addition, although the pulse wave is measured by decreasing the applied pressure from the arterial diastolic pressure in the third embodiment, the pulse wave may be measured by increasing the applied pressure from an appropriate pressure.

What is claimed is:

[1. A venous pressure measurement apparatus comprising:

a first cuff configured to be attached to a first portion including a vein and an artery in a living body;

a pressure control unit that changes a first applied pressure applied by said first cuff to said first portion by sending a flow of air to the first cuff;

a first pulse wave sensor that detects a first pulse wave from the pressure received by said first cuff from said first portion;

a second pulse wave sensor configured to detect a second pulse wave including at least an arterial pulse wave in a second portion different from said first portion of said living body;

a pressure waveform analyzing processor, comprising an analyzing unit that analyzes differences between said second pulse wave detected by said second pulse wave sensor and said first pulse wave detected by said first pulse wave sensor as a correlation, which are changed as said first applied pressure is changed by said pressure control unit; and a venous pressure calculation unit that calculates a venous pressure based on said first applied pressure and a result of analysis by said analyzing unit.]

[2. The venous pressure measurement apparatus as claimed in claim 1, wherein said venous pressure calculation unit calculates said venous pressure based on the first applied pressure when said correlation is minimized as a result of the analysis by said analyzing unit.]

[3. The venous pressure measurement apparatus as claimed in claim 1, wherein said analyzing unit obtains a venous pressure wave component by subtracting a component correlated with said second pulse wave from said first pulse wave.]

[4. The venous pressure measurement apparatus as claimed in claim 3, wherein the component correlated with said second pulse wave is an arterial pulse wave component of said first pulse wave calculated from an arterial pulse wave component of said second pulse wave and said first pulse wave.]

[5. The venous pressure measurement apparatus as claimed in claim 3, wherein said venous pressure calculation unit calculates said venous pressure based on said first applied pressure when an amplitude of said venous pulse wave component is maximized.]

[6. The venous pressure measurement apparatus as claimed in claim 1, wherein said first cuff is configured to be attached to an upper arm in the vicinity of a neck or an axilla.]

[7. The venous pressure measurement apparatus as claimed in claim 1, wherein said second pulse wave sensor is a second cuff configured to be attached to said second portion distal to said first cuff with respect to the heart of said living body, and said pressure control unit further controls a second applied pressure applied by said second cuff to said second portion.]

[8. The venous pressure measurement apparatus as claimed in claim 7, wherein said first cuff is configured to be attached to an upper arm in the vicinity of an axilla, and said second cuff is configured to be attached to a portion distal to said first cuff with respect to the heart in the upper arm where said first cuff is attached.]

[9. The venous pressure measurement apparatus as claimed in claim 1, wherein said second pulse wave sensor is a photoplethysmographic pulse wave sensor.]

[10. The venous pressure measurement apparatus as claimed in claim 7, wherein said pressure control unit controls such that said first applied pressure of said first cuff is equal to said second applied pressure of said second cuff.]

[11. The venous pressure measurement apparatus as claimed in claim 7, wherein said pressure control unit maintains said second applied pressure constant at a pressure equal to or higher than a venous pressure anticipated in advance.]

[12. The venous pressure measurement apparatus as claimed in claim 1, wherein the pressure waveform analyzing processor, further comprises a phase correction unit that performs correction to reduce a phase difference between said first pulse wave and said second pulse wave.]

[13. The venous pressure measurement apparatus as claimed in claim 7, further comprising:

a third cuff configured to be attached between said first cuff and said second cuff which are each configured to be attached to the same upper arm to measure an arterial pressure, wherein these three cuffs are integrated into a single unit.]

[14. The venous pressure measurement apparatus as claimed in claim 1, wherein said venous pressure calculation unit corrects the calculated venous pressure by a relation between said venous pressure measured in advance and said first applied pressure.]

*15. A venous pressure measurement apparatus comprising:*

*a cuff configured to be attached to a portion including a vein and an artery in a living body;*

*a pressure control unit that changes an applied pressure applied by said cuff to said portion;*

*a pressure sensor that detects a pulse wave from a pressure received by said cuff from said portion; and*

*an analyzing circuit that calculates a venous pressure based on the applied pressure and the pulse wave, which is changed as the applied pressure is changed by said pressure control unit, detected by the pressure sensor;*

*wherein calculating the venous pressure includes comparing a reference pulse wave detected by said pressure sensor when a reference pressure higher than a venous pressure anticipated in advance is set to said applied pressure and said pulse wave detected by said pressure sensor when a pressure lower than said reference pressure is set to said applied pressure.*

*16. A venous pressure measurement method comprising:*

*changing an applied pressure applied by a cuff, which is attached to a portion including a vein and an artery in a living body, to said portion;*

*detecting a pulse wave from a pressure received by said cuff from said portion; and*

*calculating a venous pressure based on the applied pressure and the detected pulse wave which is changed as the applied pressure is changed;*

*wherein the calculating the venous pressure includes comparing a reference pulse wave detected when a reference pressure higher than a venous pressure anticipated in advance is set to said applied pressure and said pulse wave detected when a pressure lower than said reference pressure is set to said applied pressure.*

* * * * *